United States Patent
Moretz

(10) Patent No.: US 9,498,415 B2
(45) Date of Patent: Nov. 22, 2016

(54) METHOD OF COUNTERING RESIDUAL MOUTH ALCOHOL

(71) Applicant: BREATHALYZER EQUALIZER, LLC, Atlanta, GA (US)

(72) Inventor: McCoy Moretz, Beverly Hills, CA (US)

(73) Assignee: Breathalyzer Equalizer, LLC, Atlanta, GA (US)

( * ) Notice: Subject to any disclaimer, the term of this patent is extended or adjusted under 35 U.S.C. 154(b) by 0 days.

(21) Appl. No.: 15/061,665

(22) Filed: Mar. 4, 2016

(65) Prior Publication Data

US 2016/0184198 A1    Jun. 30, 2016

Related U.S. Application Data

(62) Division of application No. 13/767,664, filed on Feb. 14, 2013, now abandoned.

(60) Provisional application No. 61/730,332, filed on Nov. 27, 2012.

(51) Int. Cl.
*A61K 8/19* (2006.01)
*A61K 8/97* (2006.01)
*A61Q 11/00* (2006.01)
*G01N 1/34* (2006.01)

(52) U.S. Cl.
CPC . *A61K 8/19* (2013.01); *A61K 8/97* (2013.01); *A61K 8/975* (2013.01); *A61Q 11/00* (2013.01); *G01N 1/34* (2013.01); *A61K 2800/5922* (2013.01)

(58) Field of Classification Search
CPC .......... A61K 8/19; A61K 8/97; A61K 8/975; A61Q 11/00; G01N 1/34
See application file for complete search history.

(56) References Cited

U.S. PATENT DOCUMENTS 5,885,556 A   3/1999   Lukacovic
8,227,513 B2  7/2012   Suovaniemi et al.

FOREIGN PATENT DOCUMENTS

| WO | 9933437 A1 | 7/1999 | |
|----|----|----|----|
| WO | 2007136284 A1 | 11/2007 | |
| WO | 2010121323 A1 | 10/2010 | |
| WO | 2012100991 A1 | 8/2012 | |
| WO | WO 2012100991 A1 * | 8/2012 | ........... A23L 1/3014 |

OTHER PUBLICATIONS

Ron Lloyd Breathalyzer Equalizer Demo Beer [video], Jul. 22, 2012, Breathalyzer Equalizer, http://www.youtube.com/watch?v=MUxpjfQipel.

Thomas, Shane, PCT Notification of Transmittal of the International Search Report and the Written Opinion of the International Searching Authority, or the Declaration, Mar. 28, 2014.

* cited by examiner

*Primary Examiner* — Michael B Pallay
(74) *Attorney, Agent, or Firm* — Stetina Brunda Garred & Brucker

(57) ABSTRACT

A residual mouth alcohol inhibitor configured as an oral composition that absorbs residual mouth alcohol that remains in the mouth of an individual following the consumption of alcohol. The oral composition comprises a combination of sodium bicarbonate, calcium carbonate, parsley, kelp, fructose, citric acid, natural flavors, artificial flavors, maltodextrin, and silicon dioxide whereby the ratio of sodium bicarbonate to calcium carbonate in the composition is approximately 1:1 and the ratio of sodium bicarbonate to parsley in the composition is approximately 2:1 and the ratio of parsley to kelp in the composition is approximately 4:1.

10 Claims, No Drawings

METHOD OF COUNTERING RESIDUAL MOUTH ALCOHOL

CROSS-REFERENCE TO RELATED APPLICATIONS

This application is a divisional application of U.S. application Ser. No. 13/767,664, filed on Feb. 14, 2013, which claims the benefit of U.S. Provisional Application No. 61/730,332, filed on Nov. 27, 2012, the contents of which are expressly incorporated herein by reference.

STATEMENT RE: FEDERALLY SPONSORED RESEARCH/DEVELOPMENT

Not Applicable

BACKGROUND

The present invention relates to food grade oral compositions that facilitate the absorption of methyl group structure compositions. More specifically, the present invention relates to food grade oral compositions that absorb residual mouth alcohol present after alcohol ingestion.

Alcohol abuse is a national problem that extends into virtually all aspects of society. Current practice for alcohol measurements to detect alcohol abuse is typically based upon either blood measurements or breath testing. Blood measurements are generally considered the "gold standard" for determining alcohol intoxication levels. However, blood measurements typically require either a venous or capillary sample and involve significant handling precautions in order to minimize health risks. Once extracted, the blood sample must be properly labeled and transported to a clinical laboratory or other suitable location where a clinical gas chromatograph is typically used to measure the blood alcohol level. Due to the invasiveness of the procedure and the amount of sample handling involved, blood alcohol measurements are usually limited to critical situations such as for traffic accidents, violations where the suspect requests this type of test, and accidents where injuries are involved.

Because it is less invasive, breath testing is more commonly encountered in the field. In breath testing, the subject must expire air into the instrument for a sufficient time and volume to achieve a stable breath flow that originates from alveoli deep within the lungs. The device then measures the alcohol content in the air, which is related to blood alcohol through a blood-breath ratio (BBR). The blood-breath ratio used in the United States is 2100 and varies between 1900 and 2400 in other nations. The variability in the BBR is due to the fact that it is dependent on each person's physiology. In other words, each subject will generally have a BBR in the 1900 to 2400 range depending on his or her physiology, since knowledge of each subject's BBR is unavailable in field applications, each nation assumes a single partition coefficient value that is globally applied to all measurements. In the U.S., defendants in DUI cases often use the globally applied BBR as an argument to impede prosecution.

Currently breath analysis, in the form of breath measurements, is performed by breath analyzers (Breathalyzer, Intoxilyzer, Alcosensor, Alcoscan and BAC Datamaster are common brand names) which have been shown to have serious limitations. As a preliminary matter, breath analyzers estimate blood alcohol content indirectly. Different types of machines use different techniques and larger machines generally yield better estimates than do hand-held models. Therefore, some states don't permit data or "readings" from hand-held machines to be presented as evidence in court. South Dakota does not even permit evidence from any type or size breath tester but relies entirely on blood tests to ensure accuracy and protect the innocent.

A major problem with some breath analyzer machines is that they not only identify the ethyl alcohol (or ethanol) found in alcohol beverages, but also other substances similar in molecular structure. Those machines identify any compound containing the methyl group structure. Over one hundred compounds can be found in the human breath at any one time and 70 to 80 percent of them contain methyl group structure and will be incorrectly detected as ethyl alcohol. This fact adds serious complexity to field sobriety testing conducted with breath analyzer machines because the more different ethyl group substances the machine detects, the higher will be the false blood alcohol content estimate. This may lead to higher estimated blood alcohol content readings than are accurate and cause a subject being tested to render a breath analysis reading that indicates that they are operating a vehicle with blood alcohol content that is higher than the legal limit; commonly referred to as a false positive.

In addition to the numerous compounds that can be found in the human breath that may incorrectly elevate an alcohol content reading, the presence of "mouth alcohol" can further elevate the breath alcohol measurement, pushing a subject who may not technically be operating a motor vehicle with a blood alcohol content higher than the legal limit to yield blood alcohol content levels that are higher than the legal limit when a subject is tested by way of breath analysis in the field. Currently the issue of "mouth alcohol" is dealt with by implementing a 15-minute waiting period prior to making a breath measurement in order to ensure that none or substantially low levels of mouth alcohol is present. For a similar reason, a 15-minute delay is required before a breath alcohol test may be administered in the field upon individuals who are observed to burp or vomit just prior to breath analysis testing. However, it is difficult to assess whether a subject being tested has burped within a 15-minute period prior to an actual field breath analysis test, causing ambiguity and questions regarding the accuracy of breath analysis field sobriety testing. A delay of 10 minutes or more is often required between breath measurements to allow the instrument to return to equilibrium with the ambient air and zero alcohol levels.

There is a need for an improved method of field testing that reduces the probability of false positive tests indicating that a subject who may not technically have an actual blood alcohol content level that is higher than the legal limit to yield false blood alcohol content level readings reflecting that the subject does in fact have an actual blood alcohol content level that is higher than the legal limit. There is also a need for an improved method of field sobriety testing that removes the disadvantages of the breath BBR and inaccurate field readings resulting from residual mouth alcohol and those resulting from breath analyzer machines that identify substances similar in molecular structure to that of ethyl alcohol (or ethanol).

BRIEF SUMMARY

Consistent with embodiments of the present invention, an aspect of the present invention comprises a food consumable product and method that enables breath analysis machines, which estimate a test subject's blood alcohol content indirectly, to render more accurate readings regarding the prior ingestion of alcohol. The food consumable product facilitates a method of inhibiting residual mouth alcohol that remains in the mouth of an individual following alcohol consumption. The oral composition comprises a combination of sodium bicarbonate, calcium carbonate, parsley, kelp, fructose, citric acid, natural flavors, artificial flavors, maltodextrin, and silicon dioxide whereby the ratio of sodium bicarbonate to calcium bicarbonate in the composition is approximately 1:1 and the ratio of sodium bicarbonate to parsley in the composition is approximately 2:1 and the ratio of parsley to kelp in the composition is approximately 4:1.

It is to be understood that both the foregoing summary of the invention and the following detailed description are exemplary and explanatory only, and should not be considered restrictive of the scope of the invention, as described and claimed. Further, features and/or variations may be provided in addition to those set forth herein.

Consistent with embodiments of the present invention, an aspect of the present invention comprises a food consumable product and method that enables breath analysis machines, which estimate a test subject's blood alcohol content indirectly, to render more accurate readings regarding the prior ingestion of alcohol. The product and method facilitates proper use of breath analysis machines through the reduction of residual mouth alcohol and any known substances that might be contained within the oral/pharyngeal cavity that can interfere with the measurements recorded by breath analysis machines. The active ingredients in the product absorbs the ethyl alcohol (or ethanol) found in alcohol beverages, but also other substances similar in molecular structure, specifically any substances that contain compounds containing the methyl group structure. Compounds that could be present and effect the accuracy of breath analysis machines include at least: lacquer, cigarette smoke, perfumes, paint remover, celluloid, gasoline, asthma medication inhalers, yeast containing breads, cleaning fluids, especially ethers, alcohols, mouthwash and breath sprays. The food consumable product functions as an inhibitor to these compounds that could be present in the mouth of an individual following consumption by absorbing a substantial amount of residual compounds remaining in the mouth of an individual. The food consumable product comprises a combination of sodium bicarbonate, calcium carbonate, parsley, kelp, fructose, citric acid, natural flavors, artificial flavors, maltodextrin, and silicon dioxide whereby the ratio of sodium bicarbonate to calcium bicarbonate in the composition is approximately 1:1 and the ratio of sodium bicarbonate to parsley in the composition is approximately 2:1 and the ratio of parsley to kelp in the composition is approximately 4:1.

The food consumable product works particularly well in the absorption of ethyl alcohol (or ethanol) found in alcohol beverages, and also on other substances similar in molecular structure. The absorption properties provided by the food consumable product thereby facilitates an improvement in the reliability and accuracy of alcohol consumption or estimated blood alcohol level field tests by reducing the probability of false positive tests through absorption of residual mouth alcohol remaining in the mouth of a subject following alcohol consumption. The result being that the alcohol consumption or estimated blood alcohol level field tests may generate more accurate results based on the reduction of residual mouth alcohol which may artificially inflate test results.

It is common knowledge that breath analysis testing is not an exact science. On occasion, a breath analysis test incorrectly indicates that a subject has a blood alcohol content level reading that is higher than the legal limit. The present invention improves the reliability of breath analysis testing by absorbing residual mouth alcohol which may incorrectly cause the breath analysis test to yield blood alcohol content level estimates that are higher than the legal limit. The present invention provides an improved method of field sobriety testing by removing the disadvantages of the breath BBR and inaccurate field readings resulting from residual mouth alcohol and those resulting from breath analyzer machines that identify substances similar in molecular structure to that of ethyl alcohol (or ethanol).

DETAILED DESCRIPTION

Consistent with embodiments, an aspect of the present invention concerns an oral composition that is effective in removing residual mouth alcohol caused by substances ingested by a subject. The oral composition comprising the present invention is comprised of food grade ingredients that are highly absorptive and thereby effective in the removal of alcohol remaining in the mouth of a subject following alcohol consumption. The oral composition comprises ingredients that include food grade calcium and carbon molecules that are highly absorptive component of breath odor/alcohol fumes, whatever the residual substances that are in the mouth that may be contributing to inaccurate breath analysis readings. The calcium and carbon molecules within the oral composition comprising the present invention serve in a manner similar to carbon and calcium filters used in other applications such as a swimming pool or air cleaners, whereby the carbon and calcium is highly absorptive of odors or chemical substances. In additional to food grade calcium and carbon molecules, an embodiment of the oral composition that comprises the present invention includes food grade ingredients, including but not limited to parsley and kelp. The parsley which is a green leafy vegetable has chlorophyll which is included in the composition as breath freshening agent. The kelp is also a highly absorbent material, which also includes chlorophyll because kelp is also a green leafy vegetable.

In one embodiment of the present invention, the calcium molecule utilized in the present invention is Sodium Bicarbonate, a chemical compound with formula $NaHCO_3$. Sodium bicarbonate is a white solid that is crystalline but often appears as a fine powder. It has a slightly salty, alkaline taste resembling that of washing soda (sodium carbonate). The natural mineral form is nahcolite. It is a component of the mineral natron and is found dissolved in many mineral springs. Naturally occurring deposits of nahcolite ($NaHCO_3$) are found in the Eocene-age (55.8-33.9 Ma) Green River Formation, Piceance Basin in Colorado. Nahcolite was deposited as beds during periods of high evaporation in the basin. It is commercially mined using in-situ leach techniques involving dissolution of the nahcolite by heated water that is pumped through the nahcolite beds and reconstituted through a natural cooling crystallization process. Sodium bicarbonate is also used as an ingredient in some mouthwashes. It works as a mechanical cleanser on the teeth and gums, neutralizers the production of acid in the mouth and also acts as an antiseptic to help prevent infections. Since sodium bicarbonate acts as a neutralizing agent, it can be used to absorb odors.

In one embodiment of the present invention, the carbon molecule utilized in the present invention is calcium carbonate, a chemical compound with the formula $CaCO_3$. It is a common substances found in rocks in all parts of the world, and is the main component of shells of marine organisms, snails, coal balls, pearls, and eggshells. When used as an acidity regulator, anticaking agent, stabilizer, or for colour it is approved for usage in the EU, USA and Australia and New Zealand.

*Petroselinum hortense*, also known as parsley is a species of *Petroselinum* in the family Apiaceae, native to the central Mediterranean region (southern Italy, Algeria and Tunisia), naturalized elsewhere in Europe, and widely cultivated as a herb, a spice and a vegetable. It is commonly believed that when chewed, parsley can freshen bad breath, especially from eating garlic. The methanolic extract of parsley is antimicrobial. One among such time tested home remedies to temporarily reduce bad breath is the use of parsley. This has been used in various forms for many years and is favored by many people. The leaves of Parsley are rich in chlorophyll and acts as powerful neutralizer of bad breath.

Kelps are large seaweeds (algae) belonging to the brown algae (Phaeophyceae) in the order Laminariales. Through the $19^{th}$ century, the word "kelp" was closely associated with seaweeds that could be burned to obtain soda ash (primarily sodium carbonate). One of the benefits of kelp is the elimination of phlegm. It is highly absorptive and has medicinal uses. It is also considered a digestive demulcent. A demulcent is a soothing agent and it is believed that the algin in the kelp forms a layer that adheres to the walls of the stomach. It is also believed to form a seal over the top of the stomach preventing reflux.

There is no chemical reaction, no chemical process or pathway by which the ingredients within the composition are interacting with the alcohol. The ingredients are simply absorbing whatever is in the mouth into the substance itself so that when it is swallowed or expectorated it is substantially reduced in oral concentration. The residual alcohol generated in the mouth following micro burps or reflux gastric GURD are combated when a user ingests the food grade composition. Upon swallowing the composition, the calcium carbonate portion of the food grade composition absorbs the alcohol that is in the stomach or in the burp.

The oral alcohol absorption composition comprising the present invention is primarily a combination of sodium bicarbonate, calcium carbonate, parsley and kelp. The ratio of sodium bicarbonate to calcium bicarbonate in the oral alcohol absorption composition is approximately 1:1. The ratio of sodium bicarbonate to parsley in the oral alcohol absorption composition is approximately 2:1. The ratio of parsley to kelp in the oral alcohol absorption composition is approximately 4:1. More specifically, in the oral alcohol absorption composition comprising one embodiment of the invention, sodium bicarbonate comprises approximately 30%-40% of the weight by volume of the composition, calcium carbonate comprises approximately 30%-40% of the weight by volume of the composition, parsley comprises approximately 15%-25% of the weight by volume of the composition and kelp comprises approximately 1%-9% of the weight by volume of the composition. In addition to the above ingredients, the composition also includes fructose, citric acid, natural flavors, artificial flavors, maltodextrin, and silicon dioxide.

The oral composition may be configured in product form as a gum, mouthwash, candy, lozenge, powder, or oral spray. However, this list of end commercial products is not intended to be exhaustive, but an illustration of possible end commercial products utilizing the oral composition. It is also contemplated that the oral composition may be utilized in a myriad of flavors such as Lemon-Lime, Orange, Spearmint, Peppermint, Blueberry, Raspberry, Tutti-fruit, Grape fruit, Grape, Cherry Strawberry, Watermelon, Lemon, Lime, Peach, Cotton Candy, Pineapple, Cinnamon, Tangerine, Toasted Marshmallow, Tangerine, Banana, Coffee, Cappuccino, Chocolate, and Coconut. However, this list of flavors is not intended to be exhaustive, but an illustration of anticipated flavors that may be added to the possible end commercial products utilizing the oral composition. It is contemplated that the present invention may be formulated in any flavor.

In one embodiment of the invention the oral composition is implemented as a powder and sold in a small packet. For effective use, a user opens the packet and empties the oral composition powder within the packet into the mouth. The user distributes the oral composition powder evenly through oral cavity with their tongue for approximately sixty seconds before swallowing the oral composition powder. An optional step, which may enhance effectiveness of the oral composition powder, is for the consumer to rinse their mouth cavity with water for approximately fifteen seconds.

The above specification, examples and data provide a description of the manufacture and use of the invention. Since many embodiments of the invention can be made without departing from the spirit and scope of the invention, the invention resides in the claims hereinafter appended.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of countering residual mouth alcohol remaining in the mouth after alcohol consumption which consists essentially of dispersing in the oral cavity an oral composition comprising sodium bicarbonate, calcium carbonate, parsley and kelp whereby the ratio of sodium bicarbonate to calcium carbonate is approximately 1:1 and the ratio of sodium bicarbonate to parsley is approximately 2:1 and the ratio of parsley to kelp is approximately 4:1.

2. The method of claim 1 wherein the oral composition comprises 30%-40% by weight of sodium bicarbonate.

3. The method of claim 1 wherein the oral composition comprises 30%-40% by weight of calcium carbonate.

4. The method of claim 1 wherein the oral composition comprises 15%-25% by weight of parsley.

5. The method of claim 1 wherein the oral composition comprises 1%-9% by weight of kelp.

6. The method of claim 1 wherein the sodium bicarbonate comprises approximately 30%-40% of the weight by volume of the composition, calcium carbonate comprises approximately 30%-40% of the weight by volume of the composition, parsley comprises approximately 15%-25% of the weight by volume of the composition and kelp comprises approximately 1%-9% of the weight by volume of the composition.

7. The method of claim 1 further comprising the step of distributing the oral composition throughout the oral cavity using the tongue.

8. The method of claim 7 whereby the oral composition is distributed throughout the oral cavity with the tongue for approximately sixty seconds.

9. The method of claim 7 further comprising the step of swallowing the oral composition following distribution throughout the oral cavity.

10. The method of claim 7 further comprising the step of rinsing the oral cavity with water following distribution of the oral composition throughout the oral cavity.

\* \* \* \* \*